United States Patent [19]

Downing et al.

[11] 4,314,908

[45] Feb. 9, 1982

[54] PREPARATION OF REACTION MASS FOR THE PRODUCTION OF METHYLCHLOROSILANE

[75] Inventors: James H. Downing, Clarence; James E. Wells, III, Kenmore, both of N.Y.; Tom K. Ioannou, Marietta, Ohio

[73] Assignee: Union Carbide Corporation, New York, N.Y.

[21] Appl. No.: 87,798

[22] Filed: Oct. 24, 1979

[51] Int. Cl.³ .................. B01J 23/72; C22C 30/02
[52] U.S. Cl. .................................. 252/182; 75/134 S; 75/160; 252/476; 260/543 R; 528/10; 556/472
[58] Field of Search ............ 252/182, 476; 75/134 S, 75/160; 260/543 R; 528/10; 556/472

[56] References Cited

U.S. PATENT DOCUMENTS 2,380,996  8/1945  Rochow et al. ............... 528/10

*Primary Examiner*—Benjamin R. Padgett
*Assistant Examiner*—Irwin Gluck
*Attorney, Agent, or Firm*—John R. Doherty

[57] ABSTRACT

A copper catalyzed silicon reaction mass for the production of methylchlorosilane which comprises free-flowing powders or particles of silicon metal having spots of a copper-silicon alloy substantially uniformly distributed on the surface of the silicon particles, the copper constituting less than about 2% and preferably about 1.75% by weight of the catalytic mass.

17 Claims, No Drawings

PREPARATION OF REACTION MASS FOR THE PRODUCTION OF METHYLCHLOROSILANE

The present invention relates to the preparation of a free-flowing powdered silicon reaction mass for the production of methylchlorosilanes.

Methylchlorosilane monomers are made by direct reaction between fine silicon metal and methyl chloride in a fluid bed. A copper catalyst is necessary to realize a high conversion of the silicon to useful methylated products. In order to be effective, the copper must alloy with the surface of the silicon particles to form active catalytic sites.

U.S. Pat. No. 2,380,996 issued to E.G. Rochow on Aug. 7, 1945 discloses a process for preparing organosilicon halides which broadly comprises effecting reaction between a hydrocarbon halide and the silicon component of a solid, porous contact mass obtained by firing under reducing conditions a mixture of powdered silicon and a powdered metallic catalyst such as copper. Specifically, the porous contact mass can be made by molding a mixture of 98 percent powdered silicon and 2 percent powdered copper and then heating the mixture in a hydrogen atmosphere for about 20 minutes at a temperature of between about 1030° to 1080° C. to form porous sintered pellets. The particles of silicon used in the preparation of the contact mass may be as fine as 325-mesh and the copper particles approximately 400-mesh.

It is an object of the present invention to provide a novel and improved copper catalyzed silicon reaction mass for the production of methylchlorosilanes and a method for preparing such an improved reaction mass.

In accordance with the present invention, there is provided a novel and improved copper catalyzed silicon reaction mass for the production of methylchlorosilanes which comprises free-flowing powders or particles of silicon metal having spots of a copper-silicon alloy substantially uniformly distributed on the surface of the silicon particles, the copper constituting less than about 2% and preferably about 1.75% by weight of the catalytic mass.

The method for preparing the copper catalyzed silicon reaction mass in accordance with the present invention comprises blending together finely divided particles of silicon metal and copper catalyst, the catalyst having a particle size in the range of between about 2 and 5 microns, and then heating the blended mixture in a reducing atmosphere, preferably hydrogen, at a temperature in the range of between about 860° and 1080° C. The silicon and copper catalyst mixture should contain sufficient copper catalyst to produce a copper concentration of less than about 2% in the product, for example in the range of between about 0.2% and less than about 2% by weight of the mixture. Optionally, zinc powder can be blended with the silicon and copper powders such that the weight ratio of total copper/zinc is 10/1.

The copper catalyzed silicon reaction mass herein described advantageously employs less than about 2% by weight of copper compared to similar reaction masses in the prior art. It has been found that optimum results are obtained when the copper content of the mass is about 1.75%. The optimum copper concentration for manufacture of methylchlorosilane monomers is based on reaction rate and product selectivity (ratio of $Me_2SiCl_2/MeSiCl_3$ by weight). Reaction rate is a direct function of the Cu-Si alloy concentration. With more than optimum concentrations of copper as Cu-Si alloy the mass is extremely reactive and difficult to control which results in a shorter mass life, lower selectivity ratio, and lower conversion of the silicon to useful products. The selectivity ratio is unaffected at copper concentrations (as Cu-Si alloy) from 0.5% to less than 2% but decreases to unacceptable values when the concentration of copper (as Cu-Si alloy) is less than 0.2%.

The particle size and impurity of the copper catalyst are important factors in the practice of the invention. Particle size in the range of between about 2 and 5 microns with the total concentration of arsenic, antimony, bismuth, and lead less than 0.1% are necessary properties for the copper catalyst. The method of the invention is not sensitive to the source of copper catalyst meeting these specifications. Pure copper, $Cu_2O$, and CuO should be suitable. The best results are obtained when uniformly oxidized coppers ($Cu/Cu_2O/CuO$) are used. This includes cement-type or oxidized atomized copper. The smaller particle size permits the use of less copper catalyst than heretofore possible in the prior art, i.e., less than 2% by weight of copper. Two examples of uniformly oxidized copper catalyst suitable for the practice of the invention are listed.

|  | Example 1 | Example 2 |
| --- | --- | --- |
| Metallic Cu, % | 10.7 | 15.2 |
| $Cu_2O$, % | 44.1 | 71.8 |
| CuO, % | 42.1 | 4.6 |
| Total Cu, % | 83.6 | 82.7 |
| Pb, % | 0.06 | 0.03 |

It is also preferable in the practice of the present invention to include a small amount of zinc particles in the blended mixture to accelerate the formation of Cu-Si alloy. Without zinc in the blended mixture only 66% of the copper was converted to Cu-Si alloy in four hours at 1000° C. In the presence of zinc less than one hour at 1000° C. is required for complete conversion of the copper to Cu-Si alloy. The particle size of the zinc is not an important factor except to insure a homogeneous blend with the silicon and copper catalyst, both dust and coarser zinc particles worked equally well. The ratio of total copper/zinc in the blended powders is 10/1 by weight.

The treatment temperature used in the method of the present invention must be above the melting point of the copper-silicon alloy that is being formed, i.e., about 660° C. The temperature used in the method must also be below the melting point of copper, i.e., about 1080° C. in order to avoid sintering of the metallic particles. It has been found that the copper-silicon alloy formation is actually a time-temperature relationship requiring about 5 hours at 660° C. and only about ½ hour at about 1000° C. to achieve nearly 100% conversion of the copper catalyst to the copper-silicon alloy.

In the practice of the present invention, the silicon, copper, and optionally zinc particles can be blended in any effective commercial blender for powders, a twin-shell blender, for example. The treatment of the blended mixture can be carried out continuously in an indirect-fired rotary calciner equipped to handle countercurrent gas flow to solids flow. The minimum retention time in the calciner at a temperature of 1000° C. should be about 30 minutes and the gas velocity at this temperature should be in the range of between about 0.04 and 0.13 feet per second. A hydrogen stoichiometry in the range of between 5 and 200 to 1 should be employed. The treatment of the blend can also be carried out on a batch basis by passing hydrogen gas over a bed of the blended mix. The conditions noted for the continuous method also apply to the batch method.

In one example of the present invention, a copper catalyzed silicon reaction mass was prepared by blending 97.06 parts by weight of silicon particles (65×150 mesh), 2.7 parts by weight of cement-type copper (uniformly oxidized containing 10.9% metallic copper, 43.9% $Cu_2O$, 43.9% CuO, and 84.9% total copper), and 0.24 part by weight of zinc dust together in a twin-shell blender. The blended powders were treated in a 6½ inch diameter rotary cylinder, indirect-fired operating under the conditions shown in the following Table I. The copper catalyzed silicon reaction mass from the calciner analyzed 1.56% by weight total copper of which 90% was in the form of Cu-Si alloy. The same copper catalyzed silicon mass was then reacted with methyl chloride to make methylchlorosilanes in a 1-inch diameter carbon steel fluidized bed reactor operating at 320° C. and 60 psig. The rate of crude methylchlorosilane production and selectivity ratio for the same copper catalyzed silicon reaction mass were 31.1 grams per hour and 14.0, respectively. Equivalent results might be obtained by prior art if 7% copper is present in the reaction mass.

TABLE I

| Externally Prepared Si/Cu Masses In A Rotary Kiln | |
|---|---|
| Preparation Conditions: 6-½ Inch, Ni-Cr Rotary Kiln | |
| Si Conc., % | 97.06 |
| Catalyst Conc. | 2.7 |
| Zn Conc., % | 0.24 |
| Temperature, °C. | 1000 |
| Mass Feed, Gm/Hr | 1200 |
| Mass Discharge, Gm/Hr | 1030 |
| Kiln Loading, % Volume | 5.3 |
| Residence Time, Minutes | 61 |
| $H_2$ Flow, cc/Minute | 4800 |
| Inert Flow, cc/Minute | 0 |
| Gas Velocity at T, Ft/Sec | 0.06 |
| $H_2$:CuO | 30:1 |
| Mass Properties | |
| Total Cu, % | 1.56 |
| Alloyed Cu, % | 1.40 |
| Evaluation: 1-Inch Carbon Steel Fluidized Bed Reactor | |
| Avg Temperature, °C. | 320 |
| Avg Psig | 60 |
| Avg Di/Tri | 14.0 |
| Avg Rate, Gm/Hr | 31.1 |
| Zn Added | Yes |

The copper catalyzed silicon prepared in accordance with the present invention possesses the following advantages over the prior art. There is essentially no induction period in the process for producing methylchlorosilane monomers, less copper catalyst is required, a higher rate of reaction and selectivity ratio may be obtained, and more silicon is converted to useful products. In addition, the reaction to produce methylchlorosilanes is more stable and less sensitive to the source of the copper catalyst.

What is claimed is:

1. A copper-catalyzed silicon reaction mass for the production of methylchlorosilanes which comprises freeflowing particles of silicon metal having spots of a copper-silicon alloy substantially uniformly distributed on the surface of the silicon particles, the copper constituting less than about 2% by weight of the catalytic mass.

2. A method for preparing a coppercatalyzed silicon reaction mass which comprises blending together finely-divided particles of silicon metal and a copper catalyst, the copper catalyst having a particle size in the range of between about 2 and 5 microns, and then heating the blended mixture in a reducing atmosphere at temperatures ranging from about 660° C. to about 1080° C. for a period of from about 5 hours at lower temperatures to about one-half hour at higher temperatures, the silicon and copper catalyst mixture containing sufficient copper catalyst to produce a copper concentration of less than about 2% by weight in the product.

3. A method according to claim 2 wherein said copper catalyst mixture contains sufficient copper catalyst to produce a copper concentration of about 1.75% by weight in the product.

4. A method according to claim 2 wherein said silicon and copper catalyst mixture contains zinc powders in a weight ratio of total copper to zinc of about 10/1.

5. A method according to claim 2 wherein said copper catalyst contains arsenic, antimony, bismuth and lead in a total concentration of less than about 0.1% by weight.

6. A method according to claim 2 wherein said copper catalyst is essentially pure copper metal.

7. A method according to claim 2 wherein said copper catalyst is $Cu_2O$.

8. A method according to claim 2 wherein said copper catalyst is CuO.

9. A method according to claim 2 wherein said copper catalyst is uniformly oxidized $Cu/Cu_2O$/CuO.

10. A method according to claim 2 wherein said reducing atmosphere is hydrogen.

11. A method according to claim 10 wherein the hydrogen stoichiometry is maintained in the range of between about 5 and 20 to 1.

12. A method according to claim 2 wherein said finely-divided particles of silicon metal and copper catalyst are blended together in a rotary calciner and wherein a reducing gas is passed countercurrently to the flow of said particles through said rotary calciner.

13. A method according to claim 12 wherein said reducing gas is hydrogen.

14. A method according to claim 13 wherein the hydrogen stoichiometry is maintained in the range of between about 5 and 200 to 1.

15. A method according to claim 13 wherein said hydrogen gas flows through said rotary calciner at a velocity of between about 0.04 and 0.13 feet per second.

16. A method for preparing a copper-catalyzed silicon reaction mass which comprises blending together finely-divided particles of silicon metal, a copper catalyst and zinc powders, the copper catalyst having a particle size in the range of between 2 and 5 microns, and passing the blended mixture through a rotary calciner while continuously contacting the blended mixture with a countercurrent flow of hydrogen gas at a temperature of about 1000° C. for a period of at least about one-half hour, the silicon and copper catalyst mixture containing sufficient copper catalyst to produce a copper concentration of less than about 2% by weight in the product.

17. A method according to claim 16 wherein the hydrogen stoichiometry is maintained in the range of between about 5 and 200 to 1.

* * * * *

UNITED STATES PATENT AND TRADEMARK OFFICE
CERTIFICATE OF CORRECTION

PATENT NO. : 4,314,908

DATED : February 9, 1982

INVENTOR(S) : James H. Downing; James E. Wells, III; Tom K. Ioannou

It is certified that error appears in the above-identified patent and that said Letters Patent are hereby corrected as shown below:

Column 3, line 16, delete the word "cylinder" and substitute therefor --calciner--.

Column 4, line 38, change the number "20" to --200--.

Signed and Sealed this

Eighteenth Day of June 1985

[SEAL]

Attest:

DONALD J. QUIGG

Attesting Officer     Acting Commissioner of Patents and Trademarks